US008304407B2

(12) United States Patent
Doherty et al.

(10) Patent No.: US 8,304,407 B2
(45) Date of Patent: Nov. 6, 2012

(54) 8-SUBSTITUTED BENZOAZEPINES AS TOLL-LIKE RECEPTOR MODULATORS

(75) Inventors: George A. Doherty, Libertyville, IL (US); Charles Todd Eary, Longmont, CO (US); Robert D. Groneberg, Boulder, CO (US); Zachary Jones, Broomfield, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

(21) Appl. No.: 13/414,579

(22) Filed: Mar. 7, 2012

(65) Prior Publication Data
US 2012/0165317 A1    Jun. 28, 2012

Related U.S. Application Data

(62) Division of application No. 12/064,193, filed as application No. PCT/US2006/032098 on Aug. 17, 2006, now Pat. No. 8,153,622.

(60) Provisional application No. 60/710,004, filed on Aug. 19, 2005.

(51) Int. Cl.
*A61P 37/00* (2006.01)
*A61K 31/55* (2006.01)
*C07D 223/16* (2006.01)
*C07D 403/10* (2006.01)

(52) U.S. Cl. .............. 514/212.02; 514/213.01; 540/543; 540/593

(58) Field of Classification Search ............ 514/212.02, 514/213.01; 540/543, 593
See application file for complete search history.

(56) References Cited

U.S. PATENT DOCUMENTS

| | | | |
|---|---|---|---|
| 4,002,610 | A | 1/1977 | Mohrbacher et al. |
| 6,043,238 | A | 3/2000 | Cooper et al. |
| 2005/0096259 | A1 | 5/2005 | Tomai et al. |
| 2005/0171072 | A1 | 8/2005 | Tomai et al. |
| 2005/0226878 | A1 | 10/2005 | Tomai et al. |
| 2008/0306050 | A1 | 12/2008 | Doherty et al. |
| 2010/0216989 | A1 | 8/2010 | Howbert et al. |
| 2011/0092485 | A1 | 4/2011 | Howbert et al. |
| 2011/0118235 | A1 | 5/2011 | Howbert et al. |

FOREIGN PATENT DOCUMENTS

| | | |
|---|---|---|
| JP | 1087631 | 4/1998 |
| WO | 2004096134 A2 | 11/2004 |
| WO | WO 2005/007672 | 1/2005 |
| WO | 2006026760 A3 | 3/2006 |
| WO | WO 2007/040840 | 4/2007 |

OTHER PUBLICATIONS

Ghosh, Tarun K. et al., Toll-like receptor (TLR) 2-9 agonists-induced cytokines and chemokines: I. Comparison with T cell receptor-induced responses, Cell Immunology, 2006, 48-57, 243 ScienceDirect, St. Paul, MN.
Gerster, John F. et al., Synthesis and Structure-Activity-Relationships of 1H-Imidazo[4,5-c]quinolines That Induce Interferon Production, J Medicinal Chemistry, Sep. 29, 2004, pp. A-K.
Toll-like receptor therapies compete to reduce side effects, Nature Biotechnology, Mar. 2006, 230-231, 24, Nature Publishing Group.
Lan, Tao et al., Stabilized immune modulatory RNA compounds as agonists of Toll-like receptors 7 and 8, PNAS, Aug. 21, 2007, 104, 34, 13750-13755, The National Academy of Sciences of the USA.
International Search Report corresponding to PCT Application No. PCT/US2006/032098. Mar. 1, 2007.
Written Opinion corresponding to PCT Application No. PCT/US2006/032098 mailed Mar. 14, 2007.
Breslin, Henry J. et al., Synthesis and Anti-HIV Activity of 1,3,4,5-Tetrahydro-2H-1,4-benzodiazepin-2-one (TBO) Derivatives. Truncated 4,5,6,7-Tetrahydro-5-methylimidazo[4,5,1-jk][1,4]benzodiazepin-2(1H)-ones (TIBO) Analogues, BioOrganic & Medicinal Chemistry, 1999, 2427-2436, 7, Elsevier Science Ltd.
Hemmi, Hiroaki et al., Small anti-viral compounds active immune cells via the TLR7. MyD88-dependent signaling pathway, Nature Immunology, Feb. 2002, 196-200, vol. 3 No. 2, Nature Publishing.
Jurk, Marion et al., Human TLR7 or TLR8 independently confer responsiveness to the antiviral compound R-848, Nature Immunology, Jun. 2002, 499, vol. 3 No. 6, Nature Publishing.
Papageorgiou, Christos et al., A Non-Peptide Ligand for the Somatostatin Receptor Having a Benzodiazepinone Structure, BioOrganic & Medicinal Chemistry, Feb. 6, 1996, 267-272, vol. 6 No. 3, Elsevier Science Ltd.
Examiner's First Report to corresponding Australian Application No. 2006283620 dated May 15, 2011.
Office Action to corresponding Chinese Application No. 200680038096.4 dated Oct. 8, 2010.
Office Action to corresponding Eurasion Application No. 201377, translation attached. Mar. 19, 2008.
1st Examination Report to corresponding European Patent Application No. 06801705.2, dated Jul. 27, 2009.
2nd Examination Report to corresponding European Patent Application No. 06801705.2, dated Jul. 6, 2010.
1st Examination Report to corresponding New Zealand Patent Application No. 565907, dated Dec. 1, 2009.
2nd Examination Report to corresponding New Zealand Patent Application No. 565907, dated Mar. 14, 2011.
Office Action to corresponding Philippine Application No. 1-2008-500441, dated Mar. 16, 2011.
Office Action for Japanese Application No. 2008-527127, with translation, dated Jun. 5, 2012, 7 pages.

*Primary Examiner* — Brenda Coleman
(74) *Attorney, Agent, or Firm* — John R. Moore; Corey M. Williams; Viksnins Harris & Padys

(57) ABSTRACT

Provided are compositions and methods useful for modulation of signaling through the Toll-like receptors TLR7 and/or TLR8. The compositions and methods have use in the treatment of autoimmunity, inflammation allergy, asthma, graft rejection, graft versus host disease, infection, sepsis, cancer and immunodeficiency.

20 Claims, 3 Drawing Sheets

8-SUBSTITUTED BENZOAZEPINES AS TOLL-LIKE RECEPTOR MODULATORS

RELATED APPLICATIONS

This application is a Divisional under 37 C.F.R. 1.53(b) of U.S. Ser. No. 12/064,193, filed Feb. 19, 2008, now U.S. Pat. No. 8,153,622 issued Apr. 10, 2012, which is an application filed under 35 U.S.C. 371 from PCT Application No. PCT/US2006/032098 filed Aug. 17, 2006 which claims the benefit under 35 U.S.C. §119 of U.S. provisional patent application No. 60/710,004, filed Aug. 19, 2005, the contents of which are incorporated by reference in their entirety.

BACKGROUND OF THE INVENTION

1. Field of the Invention

This invention relates to methods and compositions for modulating immune function. More specifically, this invention relates to compositions and methods for modulating TLR7- and/or TLR8-mediated signaling.

2. Description of the State of the Art

Stimulation of the immune system, which includes stimulation of either or both innate immunity and adaptive immunity, is a complex phenomenon that can result in either protective or adverse physiologic outcomes for the host. In recent years there has been increased interest in the mechanisms underlying innate immunity, which is believed to initiate and support adaptive immunity. This interest has been fueled in part by the recent discovery of a family of highly conserved pattern recognition receptor proteins known as Toll-like receptors (TLRs) believed to be involved in innate immunity as receptors for pathogen-associated molecular patterns (PAMPs). Compositions and methods useful for modulating innate immunity are therefore of great interest, as they may affect therapeutic approaches to conditions involving autoimmunity, inflammation, allergy, asthma, graft rejection, graft versus host disease (GvHD), infection, cancer, and immunodeficiency.

Toll-like receptors (TLRs) are type I transmembrane proteins that allow organisms (including mammals) to detect microbes and initiate an innate immune response (Beutler, B., Nature 2004, 430:257-263). They contain homologous cytoplasmic domains and leucine-rich extracellular domains and typically form homodimers that sense extracellular (or internalized) signals and subsequently initiate a signal transduction cascade via adaptor molecules such as MyD88 (myeloid differentiation factor 88). There is such high homology in the cytoplasmic domains of the TLRs that, initially, it was suggested that similar signaling pathways exist for all TLRs (Re, F., Strominger, J. L., Immunobiology 2004, 209:191-198). Indeed, all TLRs can activate NF-kB and MAP kinases; however, the cytokine/chemokine release profiles derived from TLR activation appears unique to each TLR. Additionally, the signaling pathway that TLRs stimulate is very similar to the pathway that the cytokine receptor IL-1R induces. This may be due to the homology that these receptors share, i.e., TIR (Toll/IL-1R homology) domains. Once the TIR domain is activated in TLRs and MyD88 is recruited, activation of the IRAK family of serine/threonine kinases results which eventually promotes the degradation of Ik-B and activation of NF-kB (Means T. K., et al. Life Sci. 2000, 68:241-258). While it appears that this cascade is designed to allow extracellular stimuli to promote intracellular events, there is evidence that some TLRs migrate to endosomes where signaling can also be initiated. This process may allow for intimate contact with engulfed microbes and fits with the role that these receptors play in the innate immune response (Underhill, D. M., et al., Nature 1999, 401:811-815). This process might also allow host nucleic acids, released by damaged tissues (for example, in inflammatory disease) or apoptosis to trigger a response via endosomal presentation. Among mammals, there are 11 TLRs that coordinate this rapid response. A hypothesis put forward years ago (Janeway, C. A., Jr., Cold Spring Harb. Symp. Quant. Biol. 1989, 54:1-13) that the innate immune response initiates the adaptive immune response through the pattern of TLR activation caused by microbes has now been substantiated. Thus, the pathogen-associated molecular patterns (PAMPs) presented by a diverse group of infectious organisms results in a innate immune response involving certain cytokines, chemokines and growth factors followed by a precise adaptive immune response tailored to the infectious pathogen via antigen presentation resulting in antibody production and cytotoxic T cell generation.

Gram-negative bacterial lipopolysaccharide (LPS) has long been appreciated as an adjuvant and immune-stimulant and as a pharmacological tool for inducing an inflammatory reaction in mammals similar to septic shock. Using a genetic approach, TLR4 was identified as the receptor for LPS. The discovery that LPS is an agonist of TLR4 illustrates the usefulness of TLR modulation for vaccine and human disease therapy (Aderem, A.; Ulevitch, R. J., Nature 2000, 406:782-787). It is now appreciated that various TLR agonists can activate B cells, neutrophils, mast cells, eosinophils, endothelial cells and several types of epithelia in addition to regulating proliferation and apoptosis of certain cell types.

To date, TLR7 and TLR8, which are somewhat similar, have been characterized as receptors for single-stranded RNA found in endosomal compartments and thus thought to be important for the immune response to viral challenge. Imiquimod, an approved topical anti-viral/anti-cancer drug, has recently been described as a TLR7 agonist that has demonstrated clinical efficacy in certain skin disorders (Miller R. L., et al., Int. J. Immunopharm. 1999, 21:1-14). This small molecule drug has been described as a structural mimetic of ssRNA. TLR8 was first described in 2000 (Du, X., et al., European Cytokine Network 2000 (September), 11(3):362-371) and was rapidly ascribed to being involved with the innate immune response to viral infection (Miettinen, M., et al., Genes and Immunity 2001 (October), 2(6):349-355).

Recently it was reported that certain imidazoquinoline compounds having antiviral activity are ligands of TLR7 and TLR8 (Hemmi H., et al. (2002) Nat. Immunol. 3:196-200; Jurk M., et al. (2002) Nat. Immunol. 3:499). Imidazoquinolines are potent synthetic activators of immune cells with antiviral and antitumor properties. Using macrophages from wildtype and MyD88-deficient mice, Hemmi et al. recently reported that two imidazoquinolines, imiquimod and resiquimod (R848), induce tumor necrosis factor (TNF) and interleukin-12 (IL-12) and activate NF-κB only in wildtype cells, consistent with activation through a TLR (Hemmi H., et al. (2002) Nat. Immunol. 3:196-200). Macrophages from mice deficient in TLR7 but not other TLRs produced no detectable cytokines in response to these imidazoquinolines. In addition, the imidazoquinolines induced dose-dependent proliferation of splenic B cells and the activation of intracellular signaling cascades in cells from wildtype but not TLR7−/− mice. Luciferase analysis established that expression of human TLR7, but not TLR2 or TLR4, in human embryonic kidney cells results in NF-κB activation in response to resiquimod. The findings of Hemmi et al. thus suggest that these imidazoquinoline compounds are non-natural ligands of TLR7 that can induce signaling through TLR7. Recently it was reported that R848 is also a ligand for human TLR8 (Jurk M., et al. (2002) *Nat. Immunol.* 3:499).

SUMMARY OF THE INVENTION

The compositions described herein are useful for modulating immune responses in vitro and in vivo. Such compositions will find use in a number of clinical applications, such as in methods for treating conditions involving unwanted immune activity, including inflammatory and autoimmune disorders.

More specifically, one aspect of this invention provides a compound of Formula I

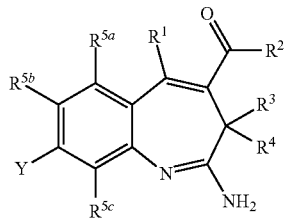

and metabolites, solvates, tautomers, and pharmaceutically acceptable salts and prodrugs thereof, wherein Y, $R^1$, $R^2$, $R^3$, $R^4$, $R^{5a}$, $R^{5b}$, and $R^{5c}$ are as defined hereinbelow.

The invention also relates to pharmaceutical compositions comprising a compound of Formula I or a solvate, pharmaceutically acceptable prodrug, metabolite, or pharmaceutically acceptable salt thereof.

The inventive compounds may be used advantageously in combination with other known therapeutic agents. Accordingly, this invention also relates to pharmaceutical compositions comprising a therapeutically effective amount of a compound of Formula I or a solvate, pharmaceutically acceptable prodrug, metabolite, or pharmaceutically acceptable salt thereof, in combination with a second therapeutic agent.

This invention further provides methods of modulating TLR7- and/or TLR8-mediated signaling, comprising contacting a cell expressing TLR7 and/or TLR8 with an effective amount of a compound of Formula I, or a solvate, pharmaceutically acceptable prodrug, metabolite, or pharmaceutically acceptable salt thereof. In one aspect, the method inhibits TLR7- and/or TLR8-mediated immunostimulatory signaling.

This invention further provides methods of modulating TLR7- and/or TLR8-mediated immunostimulation in a subject, comprising administering to a patient having or at risk of developing TLR7- and/or TLR8-mediated immunostimulation a compound of Formula I, or a solvate, pharmaceutically acceptable prodrug, metabolite, or pharmaceutically acceptable salt thereof, in an amount effective to inhibit or promote TLR7- and/or TLR8-mediated immunostimulation in the subject.

This invention further provides methods of treating a condition or disorder treatable by modulation of TLR7- and/or TLR8-mediated cellular activities, comprising administering to a warm-blooded animal, such as a mammal, for example a human, having or at risk of developing said condition or disorder a compound of Formula I, or a solvate, metabolite, pharmaceutically acceptable prodrug, or pharmaceutically acceptable salt thereof, in an amount effective to treat said condition or disorder.

This invention further provides methods of modulating the immune system of a mammal, comprising administering to a mammal a compound of Formula I, or a solvate, metabolite, pharmaceutically acceptable prodrug, or pharmaceutically acceptable salt thereof, in an amount effective to modulate said immune system.

Further provided is a compound of Formula I, or a solvate, pharmaceutically acceptable prodrug, or pharmaceutically acceptable salt thereof for use as a medicament in the treatment of the diseases or conditions described herein in a mammal, for example, a human, suffering from such disease or condition. Also provided is the use of a compound of Formula I, or a solvate, metabolite, pharmaceutically acceptable prodrug, or pharmaceutically acceptable salt thereof, in the preparation of a medicament for the treatment of the diseases and conditions described herein in a mammal, for example a human, suffering from such disorder.

This invention further provides kits comprising one or more compounds of Formula I, or a solvate, metabolite, pharmaceutically acceptable prodrug, or pharmaceutically acceptable salt thereof. The kit may further comprise a second compound or formulation comprising a second pharmaceutical agent.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

DETAILED DESCRIPTION OF THE INVENTION

Figure 1:
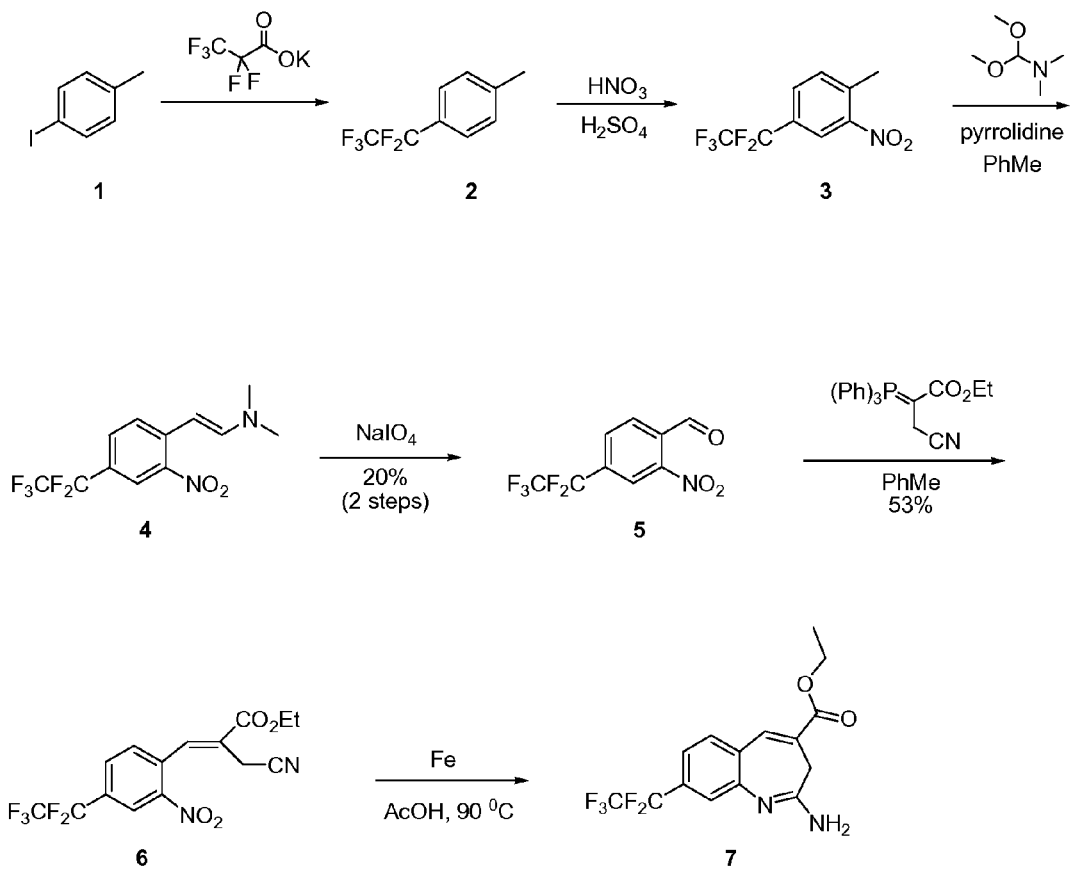
FIG. 1 shows a reaction scheme for the synthesis of compound 7.

In certain aspects, the invention provides compositions and methods useful for modulating TLR7- and/or TLR8-mediated signaling. More specifically, one aspect of this invention provides a compound of Formula I

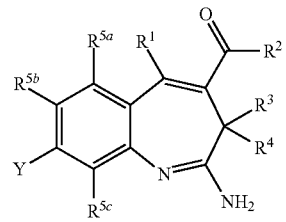

and metabolites, solvates, tautomers, and pharmaceutically acceptable salts and prodrugs thereof, wherein:

Y is $CF_2CF_3$, $CF_2CF_2R^6$, or an aryl or heteroaryl ring, wherein said aryl and heteroaryl rings are substituted with one or more groups independently selected from alkenyl, alkynyl, Br, CN, OH, $NR^6R^7$, $C(=O)R^8$, $NR^6SO_2R^7$, $(C_1$-$C_6$ alkyl)amino, $R^6OC(=O)CH=CH_2$—, $SR^6$ and $SO_2R^6$, and wherein said aryl and heteroaryl rings are optionally further substituted with one or more groups independently selected from F, Cl, $CF_3$, $CF_3O$—, $HCF_2O$—, alkyl, heteroalkyl and ArO—;

$R^1$, $R^3$ and $R^4$ are independently selected from H, alkyl, alkenyl, alkynyl, heteroalkyl, cycloalkyl, cycloalkenyl, heterocycloalkyl, aryl and heteroaryl, wherein said alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1$-$C_6$ alkyl)amino, $CH_3OCH_2O$—, $R^6OC(=O)CH=CH_2$—, $NR^6SO_2R^7$, $SR^6$ and $SO_2R^6$, or $R^3$ and $R^4$ together with the atom to which they are attached form a saturated or partially unsaturated carbocyclic ring, wherein said carbocyclic ring is optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1$-$C_6$ alkyl)amino, $CH_3OCH_2O$—, $R^6OC(=O)CH=CH_2$—, $NR^6SO_2R^7$, $SR^6$ and $SO_2R^6$;

$R^2$ and $R^8$ are independently selected from H, $OR^6$, $NR^6R^7$, alkyl, alkenyl, alkynyl, heteroalkyl, cycloalkyl, cycloalkenyl, heterocycloalkyl, aryl and heteroaryl, wherein said alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1$-$C_6$ alkyl)amino, $CH_3OCH_2O$—, $R^6OC(=O)CH=CH_2$—, $NR^6SO_2R^7$, $SR^6$ and $SO_2R^6$;

$R^{5a}$, $R^{5b}$, and $R^{5c}$ are independently H, F, Cl, Br, I, OMe, $CH_3$, $CH_2F$, $CHF_2$ or $CF_3$; and $R^6$ and $R^7$ are independently selected from H, alkyl, alkenyl, alkynyl, heteroalkyl, cycloalkyl, cycloalkenyl, heterocycloalkyl, aryl and heteroaryl, wherein said alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1$-$C_6$ alkyl)amino, $CH_3OCH_2O$—, $R^6OC(=O)CH=CH_2$—, $NR^6SO_2R^7$, $SR^6$ and $SO_2R^6$, or $R^6$ and $R^7$ together with the atom to which they are attached form a saturated or partially unsaturated heterocyclic ring, wherein said heterocyclic ring is optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1$-$C_6$ alkyl)amino, $CH_3OCH_2O$—, $R^6OC(=O)CH=CH_2$—, $NR^6SO_2R^7$, $SR^6$ and $SO_2R^6$.

In certain embodiments, $R^1$, $R^3$ and $R^4$ are each hydrogen.

In certain embodiments, $R^{5a}$, $R^{5b}$ and $R^{5c}$ are each hydrogen.

In certain embodiments of said compound of Formula I, $R^2$ is $OR^6$. In certain embodiments, $R^6$ is alkyl, such as (1-4C) alkyl. In particular embodiments, $R^6$ is ethyl.

In certain embodiments of said compound of Formula I, $R^2$ is $NR^6R^7$. In certain embodiments, $R^6$ and $R^7$ are independently H, alkyl, such as (1-6C)alkyl, or heteroalkyl, such as (1-4C)alkoxy(2-4C)alkyl. In particular embodiments, $R^6$ and $R^7$ are independently H, ethyl, propyl, or $CH_2CH_2OCH_3$.

In certain embodiments of said compound of Formula I, Y is aryl, such as phenyl. In certain embodiments, said aryl is substituted with $C(=O)R^8$, such as in para-$R^8C(=O)$phenyl. In certain embodiments, $R^8$ is $OR^6$, $NR^6R^7$ or heterocycloalkyl. In certain embodiments, $R^6$ and $R^7$ are independently H or alkyl, such as (1-6C)alkyl. In certain other embodiments, $R^6$ and $R^7$ together with the nitrogen atom to which they are attached form a 4-6 membered azacycloalkyl ring, such as pyrrolidinyl. In particular embodiments, Y is

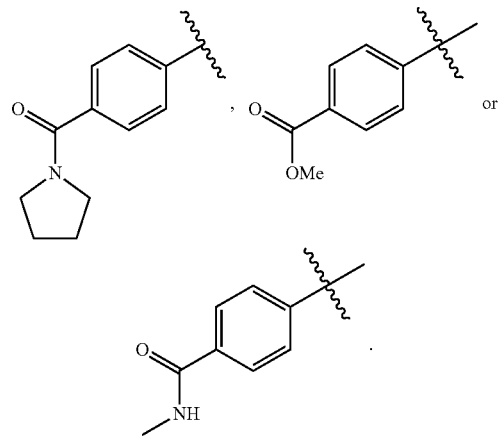

In certain embodiments of said compound of Formula I, Y is $CF_2CF_3$.

The term "alkyl" as used herein refers to a saturated linear or branched-chain monovalent hydrocarbon radical having one to twelve, including one to ten carbon atoms, one to six carbon atoms and one to four carbon atoms, wherein the alkyl radical may be optionally substituted independently with one or more substituents described below. Examples of alkyl radicals include $C_1$-$C_{12}$ hydrocarbon moieties such as, but not limited to: methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, and 1-octyl.

The term "alkenyl" refers to a linear or branched-chain monovalent hydrocarbon radical having two to 10 carbon atoms, including two to six carbon atoms and two to four carbon atoms, and at least one double bond, and includes, but is not limited to, ethenyl, propenyl, 1-but-3-enyl, 1-pent-3-enyl, 1-hex-5-enyl and the like, wherein the alkenyl radical may be optionally substituted independently with one or more substituents described herein, and includes radicals having "cis" and "trans" orientations, or alternatively, "E" and "Z" orientations. The term "alkenyl" includes allyl.

The term "alkynyl" refers to a linear or branched monovalent hydrocarbon radical of two to twelve carbon atoms, including two to 10 carbon atoms, two to six carbon atoms and two to four carbon atoms, containing at least one triple bond. Examples include, but are not limited to, ethynyl, propynyl, butynyl, pentyn-2-yl and the like, wherein the alkynyl radical may be optionally substituted independently with one or more substituents described herein.

The terms "carbocycle," "carbocyclyl," or "cycloalkyl" are used interchangeably herein and refer to saturated or partially unsaturated cyclic hydrocarbon radical having from three to twelve carbon atoms, including from three to ten carbon atoms and from three to six carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system, or as bridged systems such as bicyclo [2.2.1]heptane, bicyclo[2.2.2]octane, and bicyclo[3.2.2] nonane. The cycloalkyl may be optionally substituted independently at one or more substitutable positions with one or more substituents described herein. Such cycloalkyl groups may be optionally substituted with, for example, one or more groups independently selected from $C_1$-$C_6$ alkyl, $C_1$-$C_6$ alkoxy, halogen, hydroxy, cyano, nitro, amino, mono ($C_1$-$C_6$) alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino ($C_1$-$C_6$)alkyl, mono($C_1$-$C_6$)alkylamino($C_1$-$C_6$)alkyl and di($C_1$-$C_6$)alkylamino($C_1$-$C_6$)alkyl.

The term "cycloalkenyl" refers to a partially unsaturated cyclic hydrocarbon radical having from three to ten carbon atoms, including from three to six carbon atoms, and having at least one double bond within the carbocycle.

The term "heteroalkyl" refers to saturated linear or branched-chain monovalent hydrocarbon radical of one to twelve carbon atoms, including from one to six carbon atoms and from one to four carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The terms "heterocycloalkyl," "heterocycle" and "heterocyclyl" are used interchangeably herein and refer to a saturated or partially unsaturated carbocyclic radical of 3 to 8 ring atoms in which at least one ring atom is a heteroatom selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. The term further includes fused ring systems which include a heterocycle fused to an aromatic group. "Heterocycloalkyl" also includes radicals where heterocycle radicals are fused with aromatic or heteroaromatic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco [3.1.0]hexanyl, 3-azabicyclo[4.1.0]heptanyl, azabicyclo [2.2.2]hexanyl, 3H-indolyl quinolizinyl and N-pyridyl ureas. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, one or more groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$) alkyl.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl, etc.), which is optionally substituted with one or more substituents independently selected from, for example, halogen, lower alkyl, lower alkoxy, trifluoromethyl, aryl, heteroaryl and hydroxy.

The term "heteroaryl" refers to a monovalent aromatic radical of 5-, 6-, or 7-membered rings and includes fused ring systems (at least one of which is aromatic) of 5-10 atoms containing at least one and up to four heteroatoms selected from nitrogen, oxygen, and sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups are optionally substituted with one or more substituents independently selected from, for example, halogen, lower alkyl, lower alkoxy, haloalkyl, aryl, heteroaryl, and hydroxy.

The term "halogen" represents fluorine, bromine, chlorine, and iodine.

The term "oxo" represents =O.

In general, the various moieties or functional groups of the compounds of Formula I may be optionally substituted by one or more substituents. Examples of substituents suitable for purposes of this invention include, but are not limited to, oxo, halogen, cyano, nitro, trifluoromethyl, difluoromethoxy, trifluoromethoxy, azido, —NR"SO$_2$R', —SO$_2$NR'R", —C(O) R', —C(O)OR', —OC(O)R', —NR"C(O)OR', —NR"C(O) R', —C(O)NR'R", —NR'R", —NR'''C(O)N'R", —NR'''C (NCN)NR'R", —OR', aryl, heteroaryl, arylalkyl, heteroarylalkyl, heterocyclyl, and heterocyclylalkyl, where R', R" and R'" are independently H, alkyl, heteroalkyl, cycloalkyl, heterocycloalkyl, alkenyl, alkynyl, aryl or heteroaryl.

It is to be understood that in instances where two or more radicals are used in succession to define a substituent attached to a structure, the first named radical is considered to be terminal and the last named radical is considered to be attached to the structure in question. Thus, for example, an arylalkyl radical is attached to the structure in question by the alkyl group.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures, pure diastereomers and pure enantiomers of the Formula I. Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. Enantiomers can also be separated by use of a chiral HPLC column. Methods for the determination of stereochemistry and the separation of stereoisomers are well known in the art (see discussion in Chapter 4 of "Advanced Organic Chemistry", 4th edition, J. March, John Wiley and Sons, New York, 1992).

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

A single stereoisomer, e.g. an enantiomer, substantially free of its stereoisomer may be obtained by resolution of the racemic mixture using a method such as formation of diastereomers using optically active resolving agents (Eliel, E. and Wilen, S. *Stereochemistry of Organic Compounds*, John Wiley & Sons, Inc., New York, 1994; Lochmuller, C. H., (1975) *J. Chromatogr.*, 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: *Drug Stereochemistry, Analytical Methods and Pharmacology*, Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, for example a menthyl ester such as (−) menthyl chloroformate, in the presence of base, or Mosher ester, α-methoxy-α-(trifluoromethyl)phenyl acetate (Jacob III, (1982) *J. Org. Chem.* 47:4165), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (*Chiral Liquid Chromatography* (1989) W. J. Lough, Ed., Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

In addition to compounds of the Formula I, the invention also includes solvates, pharmaceutically acceptable prodrugs, pharmaceutically active metabolites, solvates, and pharmaceutically acceptable salts of such compounds.

The term "solvate" refers to an aggregate of a molecule with one or more solvent molecules.

A "pharmaceutically acceptable prodrug" is a compound that may be converted under physiological conditions or by solvolysis to the specified compound or to a pharmaceutically acceptable salt of such compound. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, cirtulline, homocysteine, homoserine, methyl-alanine, para-benzoylphenylalanine, phenylglycine, propargylglycine, sarcosine, methionine sulfone and tert-butylglycine. Particular examples of prodrugs of this invention include a compound of Formula I covalently joined to a phosphate residue or a valine residue.

Additional types of prodrugs are also encompassed. For instance, free carboxyl groups can be derivatized as amides or alkyl esters. As another example, compounds of this invention comprising free hydroxy groups may be derivatized as prodrugs by converting the hydroxy group into groups such as, but not limited to, phosphate ester, hemisuccinate, dimethylaminoacetate, or phosphoryloxymethyloxycarbonyl groups, as outlined in *Advanced Drug Delivery Reviews*, (1996)

19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including, but not limited to, ether, amine and carboxylic acid functionalities, or where the acyl group is an amino acid ester as described above, are also encompassed. Prodrugs of this type are described in *J. Med. Chem.*, (1996) 39:10. More specific examples include replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyl oxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate).

Free amines can also be derivatized as amides, sulfonamides or phosphonamides. All of these prodrug moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, —C(OH)C(O)OY wherein Y is H, ($C_1$-$C_6$)alkyl or benzyl, —C(OY$_0$)Y$_1$ wherein Y$_0$ is ($C_1$-$C_4$)alkyl and Y$_1$ is ($C_1$-$C_6$)alkyl, carboxy($C_1$-$C_6$)alkyl, amino($C_1$-$C_4$)alkyl or mono-N— or di-N,N—($C_1$-$C_6$)alkylaminoalkyl, —C(Y$_2$)Y$_3$ wherein Y$_2$ is H or methyl and Y$_3$ is mono-N— or di-N,N—($C_1$-$C_6$)alkylamino, morpholino, piperidin-1-yl or pyrrolidin-1-yl.

For additional examples of prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "Design and Application of Prodrugs," by H. Bundgaard p. 113-191 (1991); c) H. Bundgaard, *Advanced Drug Delivery Reviews*, (1992); 8:1-38 d) H. Bundgaard, et al., *Journal of Pharmaceutical Sciences*, (1988) 77:285; and e) N. Kakeya, et al., *Chem. Pharm. Bull.*, (1984) 32:692, each of which is specifically incorporated herein by reference.

A "pharmaceutically active metabolite" is a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art.

A "pharmaceutically acceptable salt," unless otherwise indicated, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, pheylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moieties, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl) ammonium, phenylethylbenzylamine, dibenzylethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

The present invention also provides salts of compounds of Formula I which are not necessarily pharmaceutically acceptable salts, but which may be useful as intermediates for preparing and/or purifying compounds of Formula I and/or for separating enantiomers of compounds of Formula I.

The inventive compounds may be prepared using the reaction routes and synthesis schemes as described in Scheme I, employing the techniques available in the art using starting materials that are readily available, or can be synthesized according to the methods described in the Examples and FIGS. 1-4 or using methods known in the art.

Scheme I

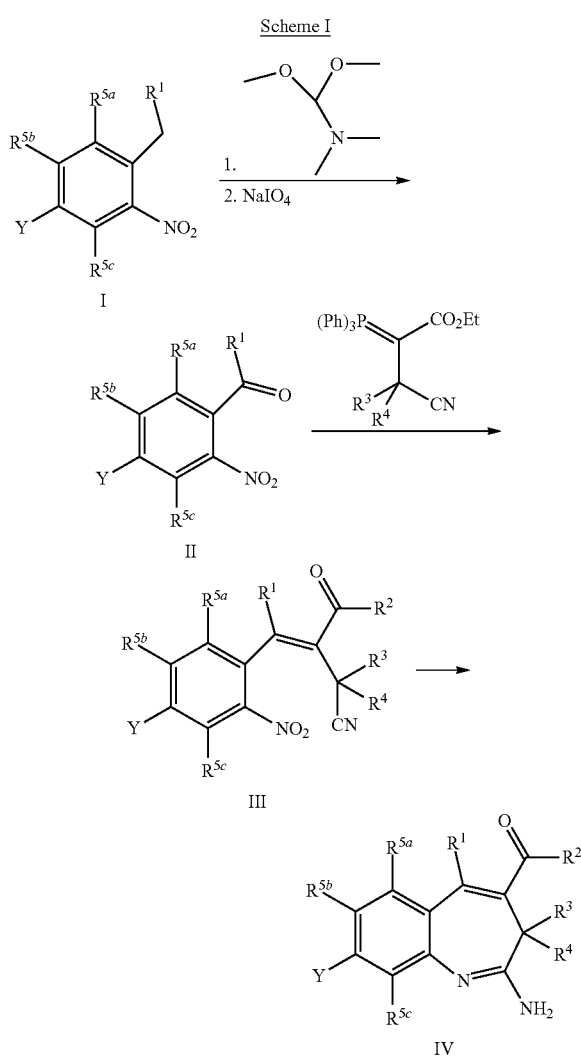

In Scheme I, compounds of Formula II may be prepared from an alkyl arene of Formula I by treatment with dimethylformamide dimethyl acetal with or without the use of pyrollidine (*J. Org. Chem.*, (1986), 51(26), 5106-5110) in DMF at 70-90° C. The crude intermediate (not shown) may be cleaved to the aldehyde of Formula II with $NaIO_4$ in THF/pH 7.2 phosphate buffer at or around room temperature. The aldehyde of Formula II may be olefinated with phosphonium ylid in toluene at temperatures ranging from 70 to 110° C. (1-16 hours) to give compounds of Formula III. Compounds of Formula IV can be prepared from a compound of Formula III using iron powder in acetic acid. The reaction may be conducted at temperatures between around 90° C. for about 3-14 hours.

It is noted that some of the preparations of compounds of Formula I described herein may require protection of remote functionalities. The need for such protection will vary depending on the nature of the functionality and the conditions used in the preparation methods and can be readily determined by those skilled in the art. Such protection/deprotection methods are well known to those skilled in the art.

The compounds of the invention find use in a variety of applications. For example, in certain aspects the invention provides methods for modulating TLR7- and/or TLR8-mediated signaling. The methods of the invention are useful, for example, when it is desirable to alter TLR7- and/or TLR8-mediated signaling in response to a suitable TLR7 and/or TLR8 ligand or a TLR7 and/or TLR8 signaling agonist.

As used herein, the terms "TLR7 and/or TLR8 ligand," "ligand for TLR7 and/or TLR8," and "TLR7 and/or TLR8 signaling agonist" refer to a molecule, other than a compound of Formula I, that interacts directly or indirectly with TLR7 and/or TLR8 through a TLR7 and/or TLR8 domain other than a TIR8 domain, and induces TLR7- and/or TLR8-mediated signaling. In certain embodiments, a TLR7 and/or TLR8 ligand is a natural ligand, i.e., a TLR7 and/or TLR8 ligand that is found in nature. In certain embodiments, a TLR7 and/or TLR8 ligand refers to a molecule other than a natural ligand of TLR7 and/or TLR8, e.g., a molecule prepared by human activity.

The term "modulate" as used herein with respect to the TLR7 and/or TLR8 receptors means the mediation of a pharmacodynamic response in a subject by (i) inhibiting or activating the receptor, or (ii) directly or indirectly affecting the normal regulation of the receptor activity. Compounds that modulate the receptor activity include agonists, antagonists, mixed agonists/antagonists and compounds that directly or indirectly affect regulation of the receptor activity.

The term "agonist" refers to a compound that, in combination with a receptor (e.g., a TLR), can produce a cellular response. An agonist may be a ligand that directly binds to the receptor. Alternatively, an agonist may combine with a receptor indirectly by, for example, (a) forming a complex with another molecule that directly binds to the receptor, or (b) otherwise resulting in the modification of another compound so that the other compound directly binds to the receptor. An agonist may be referred to as an agonist of a particular TLR (e.g., a TLR7 and/or TLR8 agonist).

The term "antagonist" as used herein refers to a compound that competes with an agonist or inverse agonist for binding to a receptor, thereby blocking the action of an agonist or inverse agonist on the receptor. However, an antagonist has no effect on constitutive receptor activity. More specifically, an antagonist is a compound that inhibits the activity of TRL7 or TLR8 at the TLR7 or TLR8 receptor, respectively.

"Inhibit" refers to any measurable reduction of biological activity. Thus, as used herein, "inhibit" or "inhibition" may be referred to as a percentage of a normal level of activity.

In one aspect of this invention, a method of treating a condition or disorder treatable by modulation of TLR7- and/or TLR8-mediated cellular activities in a subject comprises administering to said subject a composition of Formula I in an amount effective to treat the condition or disorder. The term "TLR7- and/or TLR8-mediated" refers to a biological or biochemical activity that results from TLR7- and/or TLR8 function.

Conditions and disorders that can be treated by the methods of this invention include, but are not limited to, cancer, immune complex-associated diseases, inflammatory disorders, immunodeficiency, graft rejection, graft-versus-host disease, allergies, asthma, infection, and sepsis. More specifically, methods useful in the treatment of conditions involving autoimmunity, inflammation, allergy, asthma, graft rejection, and GvHD generally will employ compounds of Formula I that inhibit TLR7- and/or TLR8-mediated signaling in response to a suitable TLR7 and/or TLR8 ligand or signaling agonist. Alternatively, methods useful in the treatment of conditions involving infection, cancer, and immunodeficiency generally will employ compounds of Formula I that augment TLR7- and/or TLR8-mediated signaling in response to a suitable TLR7 and/or TLR8 ligand. In some instances the compositions can be used to inhibit or promote TLR7- and/or TLR8-mediated signaling in response to a TLR7 and/or TLR8 ligand or signaling agonist. In other instances the compositions can be used to inhibit or promote TLR7- and/or TLR8-mediated immunostimulation in a subject.

The term "treating" as used herein, unless otherwise indicated, means at least the mitigation of a disease condition in a mammal, such as a human, and includes, but is not limited to, modulating and/or inhibiting the disease condition, and/or alleviating the disease condition to which such term applies, or one or more symptoms of such disorder or condition. The term "treatment," as used herein, unless otherwise indicated, refers to the act of treating as "treating" is defined immediately above.

As used herein, the terms "autoimmune disease," "autoimmune disorder" and "autoimmunity" refer to immunologically mediated acute or chronic injury to a tissue or organ derived from the host. The terms encompass both cellular and antibody-mediated autoimmune phenomena, as well as organ-specific and organ-nonspecific autoimmunity. Autoimmune diseases include insulin-dependent diabetes mellitus, rheumatoid arthritis, systemic lupus erythematosus, multiple sclerosis, atherosclerosis, and inflammatory bowel disease. Autoimmune diseases also include, without limitation, ankylosing spondylitis, autoimmune hemolytic anemia, Behget's syndrome, Goodpasture's syndrome, Graves' disease, Guillain-Barre syndrome, Hashimoto's thyroiditis, idiopathic thrombocytopenia, myasthenia gravis, pernicious anemia, polyarteritis nodosa, polymyositis/dermatomyositis, primary biliary sclerosis, psoriasis, sarcoidosis, sclerosing cholangitis, Sjogren's syndrome, systemic sclerosis (scleroderma and CREST syndrome), Takayasu's arteritis, temporal arteritis, and Wegener's granulomatosis. Autoimmune diseases also include certain immune complex-associated diseases.

As used herein, the terms "cancer" and, "tumor" refer to a condition in which abnormally replicating cells of host origin are present in a detectable amount in a subject. The cancer can be a malignant or non-malignant cancer. Cancers or tumors include, but are not limited to, biliary tract cancer; brain cancer; breast cancer; cervical cancer; choriocarcinoma; colon cancer; endometrial cancer; esophageal cancer; gastric (stomach) cancer; intraepithelial neoplasms; leukemias; lymphomas; liver cancer; lung cancer (e.g., small cell and non-small cell); melanoma; neuroblastomas; oral cancer; ovarian cancer; pancreatic cancer; prostate cancer; rectal cancer; renal (kidney) cancer; sarcomas; skin cancer; testicular cancer; thyroid cancer; as well as other carcinomas and sarcomas. Cancers can be primary or metastatic.

As used herein, the term "immune complex-associated disease" refers to any disease characterized by the production and/or tissue deposition of immune complexes (i.e., any conjugate including an antibody and an antigen specifically bound by the antibody), including, but not limited to systemic lupus erythematosus (SLE) and related connective tissue diseases, rheumatoid arthritis, hepatitis C- and hepatitis B-related immune complex disease (e.g., cryoglobulinemia), Behget's syndrome, autoimmune glomerulonephritides, and vasculopathy associated with the presence of LDL/anti-LDL immune complexes.

As used herein, "immunodeficiency" refers to a disease or disorder in which the subject's immune system is not functioning in normal capacity or in which it would be useful to boost a subject's immune response, for example to eliminate a tumor or cancer (e.g., tumors of the brain, lung (e.g., small cell and non-small cell), ovary, breast, prostate, colon, as well as other carcinomas and sarcomas) or an infection in a subject. The immunodeficiency can be acquired or it can be congenital.

As used herein, "graft rejection" refers to immunologically mediated hyperacute, acute, or chronic injury to a tissue or organ derived from a source other than the host. The term thus encompasses both cellular and antibody-mediated rejection, as well as rejection of both allografts and xenografts.

"Graft-versus-host disease" (GvHD) is a reaction of donated bone marrow against a patient's own tissue. GVHD is seen most often in cases where the blood marrow donor is unrelated to the patient or when the donor is related to the patient but not a perfect match. There are two forms of GVHD: an early form called acute GVHD that occurs soon after the transplant when the white cells are on the rise and a late form called chronic GVHD.

$T_{H2}$-mediated, atopic diseases include, but are not limited to, atopic dermatitis or eczema, eosinophilia, asthma, allergy, allergic rhinitis, and Ommen's syndrome.

As used herein, "allergy" refers to acquired hypersensitivity to a substance (allergen). Allergic conditions include eczema, allergic rhinitis or coryza, hay fever, asthma, urticaria (hives) and food allergies, and other atopic conditions.

As used herein, "asthma" refers to a disorder of the respiratory system characterized by inflammation, narrowing of the airways and increased reactivity of the airways to inhaled agents. Asthma is frequently, although not exclusively associated with atopic or allergic symptoms. For example, asthma can be precipitated by exposure to an allergen, exposure to cold air, respiratory infection, and exertion.

As used herein, the terms "infection" and, equivalently, "infectious disease" refer to a condition in which an infectious organism or agent is present in a detectable amount in the blood or in a normally sterile tissue or normally sterile compartment of a subject. Infectious organisms and agents include viruses, bacteria, fungi, and parasites. The terms encompass both acute and chronic infections, as well as sepsis.

As used herein, the term "sepsis" refers to the presence of bacteria (bacteremia) or other infectious organisms or their toxins in the blood (septicemia) or in other tissue of the body.

Further provided is a compound of Formula I, or a metabolite, solvate, tautomer, or pharmaceutically acceptable prodrug or salt thereof, for use as a medicament in the treatment of the diseases or conditions described above in a mammal, for example, a human, suffering from such disease or condition. Also provided is the use of a compound of Formula I, or a metabolite, solvate, tautomer, or pharmaceutically acceptable prodrug or salt thereof, in the preparation of a medicament for the treatment of the diseases and conditions described above in a mammal, for example a human, suffering from such disorder.

This invention also encompasses pharmaceutical compositions containing a compound of Formula I and methods of treating conditions and disorders treatable by modulation of TLR7- and/or TLR8-mediated cellular activities by administering a pharmaceutical composition comprising a compound of Formula I, or a metabolite, solvate, tautomer, or pharmaceutically acceptable prodrug or salt thereof, to a patient in need thereof.

In order to use a compound of Formula I or a solvate, metabolite, tautomer or pharmaceutically acceptable prodrug or salt thereof for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of Formula I, or a solvate, metabolite, tautomer or pharmaceutically acceptable prodrug or salt thereof, as defined hereinbefore in association with a pharmaceutically acceptable diluent or carrier.

To prepare the pharmaceutical compositions according to this invention, a therapeutically or prophylactically effective amount of a compound of Formula I or a solvate, metabolite tautomer or pharmaceutically acceptable prodrug or salt thereof (alone or together with an additional therapeutic agent as disclosed herein) is intimately admixed, for example, with a pharmaceutically acceptable carrier according to conventional pharmaceutical compounding techniques to produce a dose. A carrier may take a wide variety of forms depending on the form of preparation desired for administration, e.g., oral or parenteral. Examples of suitable carriers include any and all solvents, dispersion media, adjuvants, coatings, antibacterial and antifungal agents, isotonic and absorption delaying agents, sweeteners, stabilizers (to promote long term storage), emulsifiers, binding agents, thickening agents, salts, preservatives, solvents, dispersion media, coatings, antibacterial and antifungal agents, isotonic and absorption delaying agents, flavoring agents, and miscellaneous materials such as buffers and absorbents that may be needed in order to prepare a particular therapeutic composition. The use of such media and agents with pharmaceutically active substances is well known in the art. Except insofar as any conventional media or agent is incompatible with a compound of Formula I, its use in the therapeutic compositions and preparations is contemplated. Supplementary active ingredients can also be incorporated into the compositions and preparations as described herein.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. For parenteral formulations, the carrier will usually comprise sterile water, aqueous sodium chloride solution, 1,3-butanediol, or any other suitable non-toxic parenterally acceptable diluent or solvent. Other ingredients including those that aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Compositions for transdermal administration may be in the form of those transdermal skin patches that are well known to those of ordinary skill in the art.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. However, an effective dosage is in the range of about 0.001 to about 100 mg per kg body weight per day, for example, about 0.5 to about 35 mg/kg/day, in single or divided doses. For a 70 kg human, this would amount to about 0.0035 to 2.5 g/day, such as about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of Comprehensive Medicinal Chemistry (Corwin Hansch; Chairman of Editorial Board), Pergamon Press 1990, which is specifically incorporated herein by reference.

The size of the dose for therapeutic or prophylactic purposes of a compound of Formula I will naturally vary according to the nature and severity of the conditions, the age and sex of the animal or patient and the route of administration, according to well known principles of medicine. It will be understood that the specific dosage level and frequency of dosage for any particular subject may be varied and will depend upon a variety of factors including the activity of the specific compound of Formula I, the species, age, body weight, general health, sex and diet of the subject, the mode and time of administration, rate of excretion, drug combination, and severity of the particular condition, but can nevertheless be routinely determined by one skilled in the art.

A compound of Formula I will in some embodiments be administered to an individual in combination (e.g., in the same formulation or in separate formulations) with another therapeutic agent ("combination therapy"). The compound of Formula I can be administered in admixture with another therapeutic agent or can be administered in a separate formulation. When administered in separate formulations, a compound of Formula I and another therapeutic agent can be administered substantially simultaneously or sequentially.

Such combination treatment may involve, in addition to the compounds of the invention, conventional surgery or radiotherapy or chemotherapy. Such chemotherapy may include one or more of the following categories of anti-tumor agents: (i) antiproliferative/anti-neoplastic drugs and combinations thereof; (ii) cytostatic agents; (iii) agents which inhibit cancer cell invasion; (iv) inhibitors of growth factor function; (v) antiangiogenic agents; (vi) vascular damaging agents; (vii) antisense therapies; (viii) gene therapy approaches; (ix) interferon; and (x) immunotherapy approaches.

Therapeutic agents for treating respiratory diseases which may be administered in combination with a compound of Formula I in a subject method include, but are not limited to beta adrenergics which include bronchodilators including albuterol, isoproterenol sulfate, metaproterenol sulfate, terbutaline sulfate, pirbuterol acetate and salmeterol formotorol; steroids including beclomethasone dipropionate, flunisolide, fluticasone, budesonide and triamcinolone acetonide. Anti-inflammatory drugs used in connection with the treatment of respiratory diseases include steroids such as beclomethasone dipropionate, triamcinolone acetonide, flunisolide and fluticasone. Other anti-inflammatory drugs include cromoglycates such as cromolyn sodium. Other respiratory drugs which would qualify as bronchodilators include anticholenergics including ipratropium bromide. Anti-histamines include, but are not limited to, diphenhydramine, carbinoxamine, clemastine, dimenhydrinate, pryilamine, tripelennamine, chlorpheniramine, brompheniramine, hydroxyzine, cyclizine, meclizine, chlorcyclizine, promethazine, doxylamine, loratadine, and terfenadine. Particular anti-histamines include rhinolast (Astelin®), claratyne (Claritin®), claratyne D (Claritin D®), telfast (Allegra®), Zyrtec®, and beconase.

In some embodiments, a compound of Formula I is administered as a combination therapy with interferon-gamma (IFN-gamma), a corticosteroid such as prednisone, prednisolone, methyl prednisolone, hydrocortisone, cortisone, dexamethasone, betamethasone, etc., or a combination thereof, for the treatment of interstitial lung disease, e.g., idiopathic pulmonary fibrosis.

In some embodiments, a compound of Formula I is administered in combination therapy with a known therapeutic agent used in the treatment of CF. Therapeutic agents used in the treatment of CF include, but are not limited to, antibiotics; anti-inflammatory agents; DNAse (e.g., recombinant human DNAse; pulmozyme; dornase alfa); mucolytic agents (e.g., N-acetylcysteine; Mucomyst™; Mucosil™); decongestants; broncho dilators (e.g., theophylline; ipatropium bromide); and the like.

In another embodiment of the invention, an article of manufacture, or "kit", containing materials useful for the treatment of the disorders described above is provided. In one embodiment, the kit comprises a container comprising a composition of Formula I, or a metabolite, solvate, tautomer, or pharmaceutically acceptable salt or prodrug thereof. In one embodiment, the invention provides a kit for treating a TLR7- and/or TLR8-mediated disorder. In another embodiment, the invention provides a kit for a condition or disorder treatable by selective modulation of the immune system in a subject. The kit may further comprise a label or package insert on or associated with the container. Suitable containers include, for example, bottles, vials, syringes, blister pack, etc. The container may be formed from a variety of materials such as glass or plastic. The container holds a compound of Formula I or a pharmaceutical formulation thereof in an amount effective for treating the condition, and may have a sterile access port (for example, the container may be an intravenous solution bag or a vial having a stopper pierceable by a hypodermic injection needle). The label or package insert indicates that the composition is used for treating the condition of choice. In one embodiment, the label or package inserts indicates that the composition comprising a compound of Formula I can be used, for example, to treat a disorder treatable by modulation of TLR7- and/or TLR8-mediated cellular activities. The label or package insert may also indicate that the composition can be used to treat other disorders. Alternatively, or additionally, the kit may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof In another embodiment, the kits are suitable for the delivery of solid oral forms of a compound of Formula I, such as tablets or capsules. Such a kit includes, for example, a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, the kit may comprise (a) a first container with a compound of Formula I contained therein; and optionally (b) a second container with a second pharmaceutical formulation contained therein, wherein the second pharmaceutical formulation comprises a second compound which may be effective in treating a condition or disorder treatable by selective modulation of TLR7- and/or TLR8-mediated cellular activities. Alternatively, or additionally, the kit may further comprise a third container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a pharmaceutical formulation of a compound of Formula I and a second formulation comprising a second therapeutic agent, the kit may comprise a container for containing the separate formulations, such as a divided bottle or a divided foil packet; however, the separate compositions may also be contained within a single, undivided container. Typically, the kit comprises directions for the administration of the separate components. The kit form is particularly advantageous when the separate components are administered in different dosage forms (e.g., oral and parenteral), are administered at different dosage intervals, or when titration of the individual components of the combination is desired by the prescribing physician.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other compounds of the invention, and alternative methods for preparing the compounds of this invention are also deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column

Example 1

Synthesis of (1E,4E)-ethyl 2-amino-8-(perfluoroethyl)-3H-benzo[b]azepine-4-carboxylate (7)

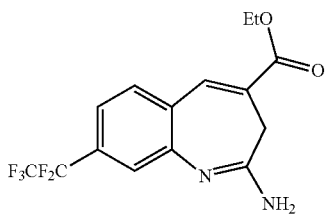

A reaction scheme for the synthesis of compound (7) is shown in FIG. 1.

Step A: Preparation of potassium 2,2,3,3,3-pentafluoropropanoate: Pentafluoropropionic acid (20.5 g, 183 mmol) was slowly added to a solution of KOtBu (29.9 g, 183 mmol) in ether (400 mL) at 0° C. After 30 minutes the ice bath was removed. After stirring at room temperature for 4 hours the suspension was filtered and the cake was washed with ether (200 mL). The fine white solid was placed under vacuum for 16 hours prior to use.

Step B: Preparation of 1-methyl-4-(perfluoroethyl)benzene (2): Procedure adapted from *Syn. Comm.*, (1988) 18(9): 965-972. A mixture of copper iodide (129 g, 679 mmol), 1-iodo-4-methylbenzene (1) (74 g, 339 mmol) and potassium 2,2,3,3,3-pentafluoropropanoate (120 g, 594 mmol) were dissolved in DMF (500 mL) and heated to 120° C. for 30 minutes and then heated at 160° C. for 4 hours, after which the mixture was allowed to cool to room temperature. Water (200 mL) and ether (200 mL) were added and after stirring for 30 minutes the solids were filtered and washed with ether. The phases were separated and the organic layer was washed with brine/water (3×250 mL). The organic layer was dried and concentrated to yield 1-methyl-4-(perfluoroethyl)benzene (66 g, 92%) as a dark oil.

Step C: Preparation of 1-methyl-2-nitro-4-(perfluoroethyl)benzene (3): Prepared from 1-methyl-4-(perfluoroethyl)benzene (1.95 g, 9.28 mmol) with sulfuric and nitric acid as described in EP 0418175 (1.45 g, 61%).

Step D: Preparation of (E)-N,N-dimethyl-2-(2-nitro-4-(perfluoroethyl)phenyl)ethenamine (4): To a solution of 1-methyl-2-nitro-4-(perfluoroethyl)benzene (10.0 g, 39.2 mmol) and pyrollidine (2.79 g, 39.2 mmol) in toluene (250 mL) was added dimethyl formamide dimethyl acetal (4.96 g, 39.2 mmol). The mixture was heated to reflux for 16 hours. After cooling to room temperature the mixture was concentrated under vacuum and the resulting oil was immediately used in the next reaction.

Step E: Preparation of 2-nitro-4-(perfluoroethyl)benzaldehyde (5): To a solution of crude (E)-N,N-dimethyl-2-(2-nitro-4-(perfluoroethyl)phenyl)ethenamine (12.2 g, 39.2 mmol) in THF (300 mL) and pH 7.2 phosphate buffer (300 mL) was added NaIO$_4$ (29.3 g, 137.2 mmol). After 2.5 hours an aliquot (~0.3 mL) was removed, filtered and dried. The proton NMR of this sample indicated that the reaction was complete. The solids were removed and the filter cake was washed with EtOAc. The filtrate was washed with brine (2×100 mL), dried and concentrated. The concentrate was purified via flash chromatography (100% hexane to 5% EtOAc) to provide 2-nitro-4-(perfluoroethyl)benzaldehyde (5.4 g, 52%).

Step F: Preparation of (E)-ethyl 2-(cyanomethyl)-3-(2-nitro-4-(perfluoroethyl)phenyl)acrylate (6): To a solution of 2-nitro-4-(perfluoroethyl)benzaldehyde (5.4 g, 20.1 mmol) in toluene (150 mL) was added α-cyanomethylcarboethoxyethylidene triphenylphosphorane (8.55 g, 22.1 mmol). The mixture was heated to 75° C. for 30 minutes. The reaction was allowed to cool and the solvent was removed under vacuum. The concentrate was purified via flash chromatography (100% hexanes to 20% EtOAc) to provide (E)-ethyl 2-(cyanomethyl)-3-(2-nitro-4-(perfluoroethyl)phenyl)acrylate (6.00 g, 79%).

Step G: Preparation of (1E,4E)-ethyl 2-amino-8-(perfluoroethyl)-3H-benzo[b]azepine-4-carboxylate (7): To a solution of (E)-ethyl 2-(cyanomethyl)-3-(2-nitro-4-(perfluoroethyl)phenyl)acrylate (2.60 g, 6.87 mmol) was added iron powder (2.30 g, 41.2 mmol). The mixture was heated to 90° C. for 5 hours. Upon cooling the acetic acid was removed under vacuum and the resulting semisolid was dissolved in 50% K$_2$CO$_3$ (100 mL) and EtOAc (100 mL). The mixture was filtered to remove insoluble material and the phases were separated. The aqueous phase was extracted with EtOAc (2×100 mL). The combined organics were dried and concentrated. The concentrate was purified via flash chromatography (100% CH$_2$Cl$_2$ to 2% MeOH) to yield (1E,4E)-ethyl 2-amino-8-(perfluoroethyl)-3H-benzo[b]azepine-4-carboxylate (1.8 g, 74%). $^1$H NMR (CDCl$_3$) δ 1.39 (t, 3H), 2.95 (s, 2H), 4.32 (q, 2H), 5.12 (br s, 1-2H), 7.22-7.27 (m, 2H), 7.47-7.51 (m, 2H), 7.80 (s, 1H).

Figure 2:
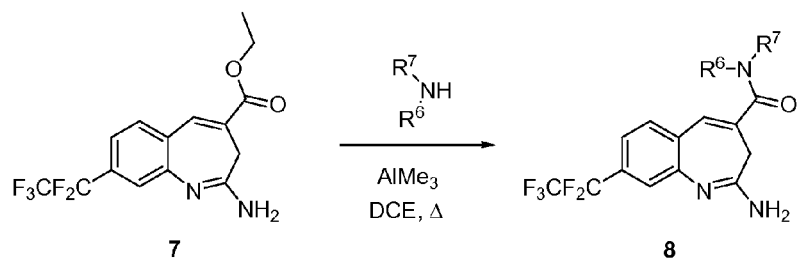
FIG. 2 shows a reaction scheme for the synthesis of compound 8.

FIG. 2 shows a reaction scheme for the synthesis of compound of the general formula (8). The following amides were prepared as shown in FIG. 2.

Example 2

Synthesis of (1E,4E)-2-amino-N,N-bis(2-methoxyethyl)-8-(perfluoroethyl)-3H-benzo[b]azepine-4-carboxamide (9)

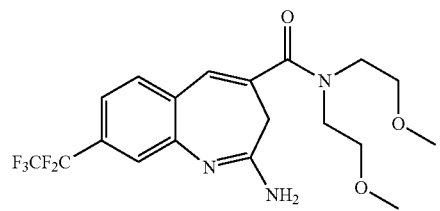

Trimethylaluminum (0.34 mL of a 2.0 M solution in toluene) was added to bis(2-methoxyethyl)amine (92 mg, 0.69 mmol) in DCE (3 mL). After 10 minutes solid (1E,4E)-ethyl 2-amino-8-(perfluoroethyl)-3H-benzo[b]azepine-4-carboxylate (80 mg, 0.23 mmol) was added and the vessel was sealed and heated to 75° C. for 16-20 hours. Upon cooling the reaction was quenched with saturated Rochelle's salt (2 mL) and after 20 minutes the mixture was partitioned between $CH_2Cl_2$ (50 mL) and brine (50 mL). The phases were separated and the aqueous was extracted with $CH_2Cl_2$ (2×20 mL). The combined organics were dried and concentrated. The crude material was purified via preparative TLC (2, 0.5 mm plates, eluting with 5-10% MeOH/$CH_2Cl_2$ with 4-6 drops of $NH_4OH$). $^1H$ NMR ($CDCl_3$) δ 2.81 (s, 2H), 3.36 (s, 6H), 3.55-3.74 (m, 8H), 6.98 (s, 1H), 7.20 (d, 1H), 7.40 (d, 1H), 7.39 (s, 1H).

Example 3

Synthesis of (1E,4E)-2-amino-N,N-diethyl-8-(perfluoroethyl)-3H-benzo[b]azepine-4-carboxamide (10)

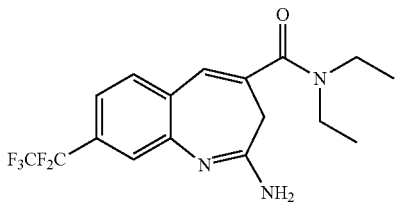

Compound (9) was prepared as described in Example 2 to provide 17 mg (21%) of the desired product. $^1H$ NMR ($CDCl_3$) δ 1.22-1.27 (m, 6H), 1.78 (s, 2H), 3.49-3.56 (m, 4H), 5.04 (br s, 1h), 6.98 (s, 1H), 7.20 (d, 1H), 7.38 (d, 1H), 7.48 (s, 1H).

Example 4

Synthesis of (1E,4E)-2-amino-8-(perfluoroethyl)-N,N-dipropyl-3H-benzo[b]azepine-4-carboxamide (11)

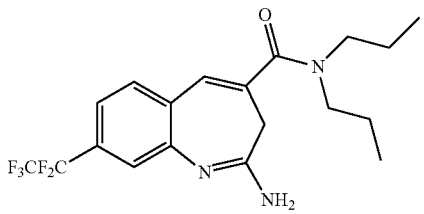

Compound (10) was prepared as described in Example 2 to provide 24 mg (28%) of the desired product. $^1H$ NMR ($CDCl_3$) δ 0.85-0.94 (m, 6H), 1.61-1.71 (m, 4H), 2.77 (s, 2H), 3.40-3.55 (m, 4H), 6.81 (s, 1H), 7.21 (d, 1H), 7.37 (d, 1H), 7.48 (s, 1H).

Figure 3:
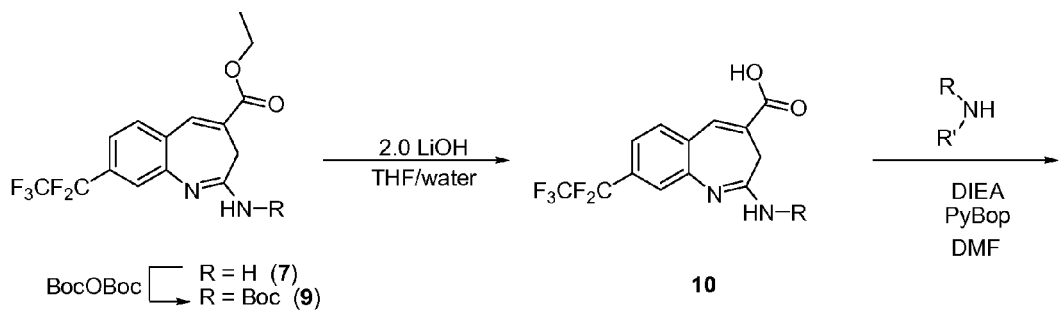
FIG. 3 shows a reaction scheme for the synthesis of compound 12.
Figure 3:
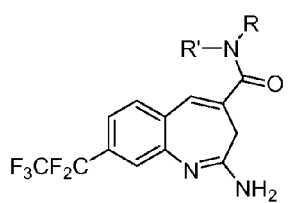
Figure 3:
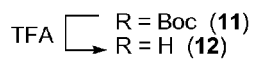

FIG. 3 shows a reaction scheme for the synthesis of compounds of the general formula (12). The following amides were prepared as shown in FIG. 3.

Example 5

Synthesis of (1E,4E)-2-amino-N-ethyl-8-(perfluoroethyl)-3H-benzo[b]azepine-4-carboxamide (15)

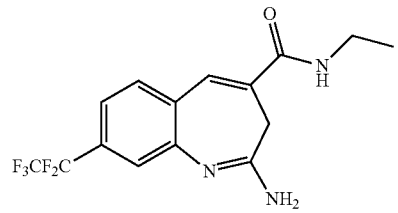

Step A: Preparation of (1E,4E)-ethyl 2-(tert-butoxycarbonyl)-8-(perfluoroethyl)-3H-benzo[b]azepine-4-carboxylate (13): To a solution of (1E,4E)-ethyl 2-amino-8-(perfluoroethyl)-3H-benzo[b]azepine-4-carboxylate (7) (2.28 g, 6.55 mmol) in $CH_2Cl_2$ (150 mL) was added Boc anhydride (1.43 g, 6.55 mmol). After 24 hours the mixture was concentrated and purified via flash chromatography (100% hexanes to 10% EtOAc) to yield (1E,4E)-ethyl 2-(tert-butoxycarbonyl)-8-(perfluoroethyl)-3H-benzo[b]azepine-4-carboxylate (1.94 g, 66%).

Step B: Preparation of (1E,4E)-2-(tert-butoxycarbonyl)-8-(perfluoroethyl)-3H-benzo[b]azepine-4-carboxylic acid (14): To a solution of (1E,4E)-ethyl 2-(tert-butoxycarbonyl)-8-(perfluoroethyl)-3H-benzo[b]azepine-4-carboxylate in THF/$H_2O$ (4:1, 10 mL) was added LiOH.$H_2O$ (42 mg, 1.00 mmol). After 4 hours the mixture was made acidic (pH 4) with 10% citric acid and extracted with $CH_2Cl_2$ (2×100 mL). The combined organics were dried and concentrated. The material was used without further purification.

Step C: Preparation of (1E,4E)-2-amino-N-ethyl-8-(perfluoroethyl)-3H-benzo[b]azepine-4-carboxamide (15): To a solution of triethylamine (76 mg, 0.750 mmol), PyBOP (143 mg, 0.275 mmol) and (1E,4E)-2-(tert-butoxycarbonyl)-8-(perfluoroethyl)-3H-benzo[b]azepine-4-carboxylic acid (105 mg, 0.250 mmol) in DMF (4 mL) was added ethylamine hydrochloride (41 mg, 0.500 mmol). After stirring for 14 hours the mixture was partitioned between EtOAc (50 mL) and brine (100 mL). The phases were separated and the organic layer was washed with water (3×100 mL). The combined organics were dried and concentrated. The crude residue was taken up in $CH_2Cl_2$/TFA (~1:1, 50 mL) and stirred at room temperature for 2 hours. The volatiles were removed under vacuum and the residue was partitioned between EtOAc and 10% $Na_2CO_3$ (1:1, 100 mL). The phases were separated and the aqueous was extracted with EtOAc (2×50 mL). The combined organics were dried and concentrated. The concentrate was purified via preparative TLC (2, 0.5 mm plates eluting with 10% MeOH/$CH_2Cl_2$ with 4-6 drops of $NH_4OH$) to provide (1E,4E)-2-amino-N-ethyl-8-(perfluoroethyl)-3H-benzo[b]azepine-4-carboxamide (6.5 mg, 8%). $^1H$ NMR ($CDCl_3$) δ 1.26 (t, 2H), 2.94 (s, 2H), 3.41-3.48 (m, 2H), 5.15 (br s, 1H), 6.08 (br s, 1H), 7.16 (s, 1H), 7.22 (d, 1H), 7.42 (d, 1H), 7.47 (s, 1H).

Example 6

Synthesis of (1E,4E)-2-amino-8-(perfluoroethyl)-N-propyl-3H-benzo[b]azepine-4-carboxamide (16)

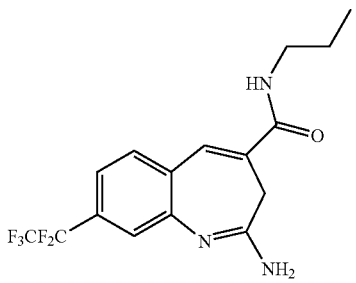

Compound (16) was prepared as described in Example 5, substituting propylamine for ethylamine hydrochloride, to provide 16 mg (45%) of the desired product. $^1$H NMR (CDCl$_3$) δ 0.99 (s, 3H), 1.59-1.68 (m, 2H), 2.94 (s, 2H), 3.34-3.92 (m, 2H), 5.19 (br s, 1H), 6.14 (br s, 1H), 7.15 (s, 1H), 7.22 (d, 1H), 7.42 (d, 1H), 7.48 (s, 1H).

Example 7

Synthesis of (1E,4E)-ethyl 2-amino-8-(4-(pyrrolidine-1-carbonyl)phenyl)-3H-benzo[b]azepine-4-carboxylate (24)

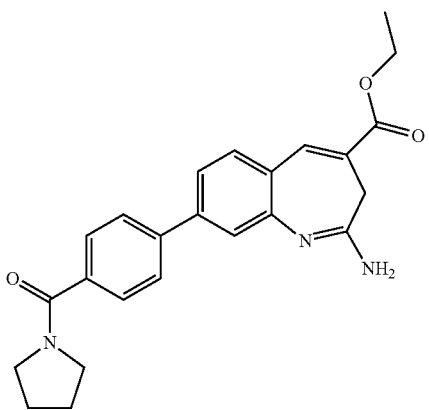

Figure 4:
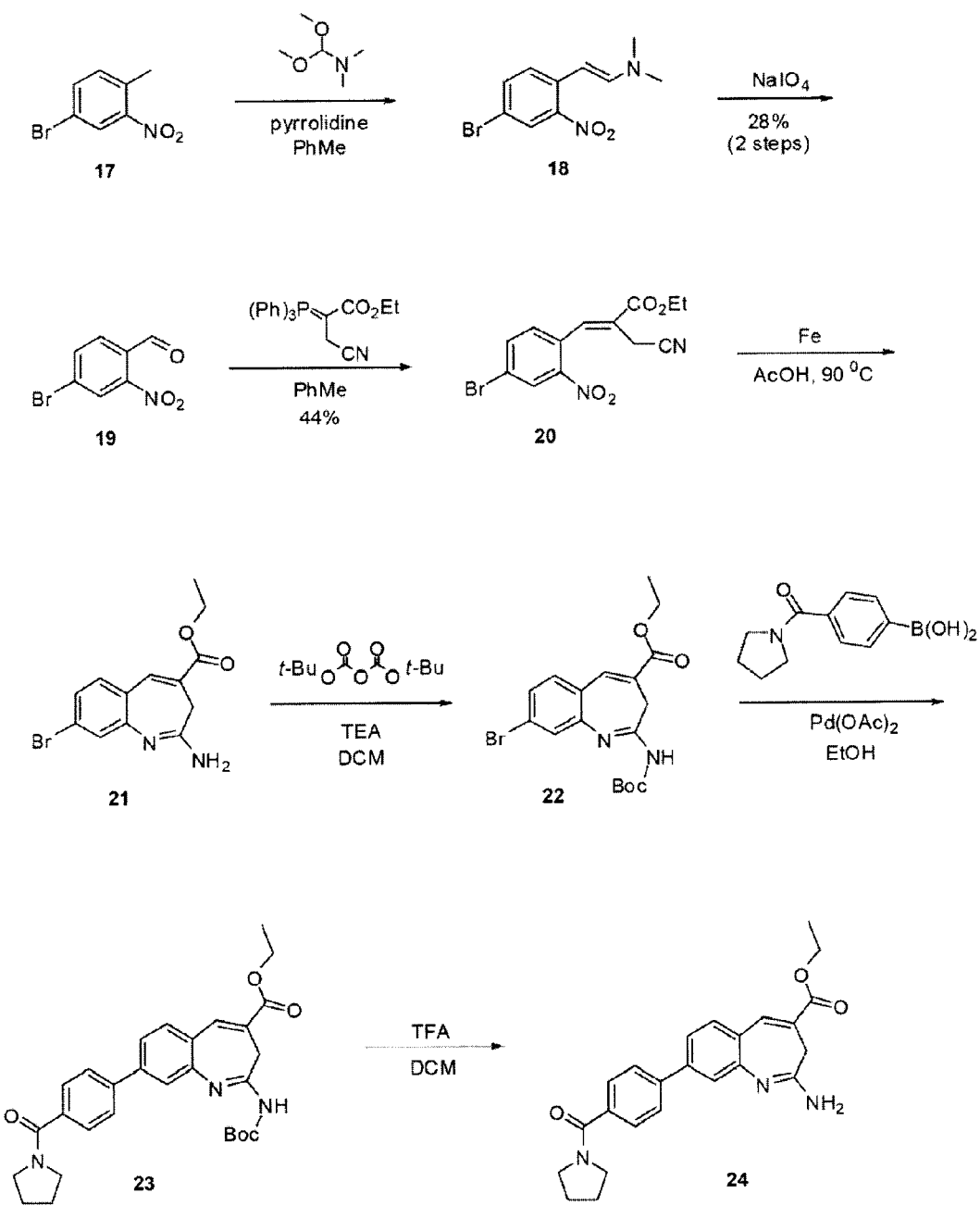
FIG. 4 shows a reaction scheme for the synthesis of compound 24.

The reaction scheme for the synthesis of compound (24) is shown in FIG. 4.

Step A: Preparation of (E)-2-(4-bromo-2-nitrophenyl)-N,N-dimethylethenamine (18): To a solution of 1-methyl-2-nitro-4-bromobenzene (17) (29.86 g, 138.2 mmol) in toluene (200 mL) was added dimethylformamide dimethylacetal (17.52 g, 138.2 mmol). The mixture was heated to reflux for 14 hours. After cooling to room temperature the mixture was concentrated under vacuum and the resulting oil was immediately used in the next reaction.

Step B: Preparation of 4-bromo-2-nitrobenzaldehyde (19): To a solution of crude (E)-2-(4-bromo-2-nitrophenyl)-N,N-dimethylethenamine (35.5 g, 131 mmol) in THF (300 mL) and pH 7.2 phosphate buffer (300 mL) was added NaIO$_4$ (56.0 g, 262 mmol). The solids were removed and the filter cake was washed with EtOAc (200 mL). The filtrate was washed with brine (2×100 mL), dried and concentrated. The concentrate was purified via flash chromatography (5% EtOAc/hexanes to 10% EtOAc/hexanes) to provide 4-bromo-2-nitrobenzaldehyde (8.41 g, 28% yield).

Step C: Preparation of (E)-ethyl 3-(4-bromo-2-nitrophenyl)-2-(cyanomethyl)acrylate (20): To a solution of 4-bromo-2-nitrobenzaldehyde (3.45 g, 15.0 mmol) in toluene (15 mL) was added α-cyanomethylcarboethoxyethylidene triphenylphosphorane (6.10 g, 15.7 mmol). The mixture was heated to 75° C. for 16 hours. The reaction was allowed to cool and the solvent was removed under vacuum. The concentrate was purified via flash chromatography (100% hexanes to 20% EtOAc) to yield (E)-ethyl 3-(4-bromo-2-nitrophenyl)-2-(cyanomethyl)acrylate (2.25 g, 44% yield) as an off white solid.

Step D: Preparation of (1E,4E)-ethyl 2-amino-8-bromo-3H-benzo[b]azepine-4-carboxylate (21): To a solution of (E)-ethyl 3-(4-bromo-2-nitrophenyl)-2-(cyanomethyl)acrylate (1.00 g, 2.9 mmol) in acetic acid (25 mL) was added iron powder (1.10 g, 19.0 mmol). The mixture was heated to 90° C. for 5 hours. Upon cooling the acetic acid was removed under vacuum and the resulting semisolid was dissolved in 50% K$_2$CO$_3$ (100 mL) and EtOAc (100 mL). The mixture was filtered to remove insoluble material and the phases were separated. The aqueous phase was extracted with EtOAc (2×100 mL). The combined organics were dried and concentrated. The concentrate was purified via flash chromatography (Biotage 40m, 5% MeOH/CH$_2$Cl$_2$) to yield (1E,4E)-ethyl 2-amino-8-bromo-3H-benzo[b]azepine-4-carboxylate (0.52 g, 57%).

Step E: Preparation of (1E,4E)-ethyl-8-bromo-2-(tert-butoxycarbonyl)-3H-benzo[b]azepine-4-carboxylate (22): To a CH$_2$Cl$_2$ (5 mL) solution containing (1E,4E)-ethyl 2-amino-8-bromo-3H-benzo[b]azepine-4-carboxylate (198 mg, 0.640 mmol) was added Boc anhydride (140 mg, 0.640 mmol). The solution was stirred at room temperature for 72 hours. The reaction was concentrated to dryness and purified by column chromatography (Biotage 12m, 4:1 hexanes:EtOAc) to provide (1E,4E)-ethyl-8-bromo-2-(tert-butoxycarbonyl)-3H-benzo[b]azepine-4-carboxylate (245 mg, 94% yield) as a white solid.

Step F: Preparation of (1E,4E)-ethyl-2-(tert-butoxycarbonyl)-8-(4-(pyrrolidine-1-carbonyl)phenyl)-3H-benzo[b]azepine-4-carboxylate (23): To an ethanol solution (15 mL) containing K$_3$PO$_4$ (938 mg, 4.42 mmol), 4-(pyrrolidine-1-carbonyl)phenylboronic acid (785 mg, 3.58 mmol), and (1E,4E)-ethyl-8-bromo-2-(tert-butoxycarbonyl)-3H-benzo[b]azepine-4-carboxylate (489 mg, 1.19 mmol), was added palladium acetate (80.5 mg, 0.358 mmol). The reaction was heated to 60° C. for 2 hours, then cooled to room temperature and concentrated to dryness. The brown oil was purified by preparative LC plate (100% EtOAc) to provide (1E,4E)-ethyl-2-(tert-butoxycarbonyl)-8-(4-(pyrrolidine-1-carbonyl)phenyl)-3H-benzo[b]azepine-4-carboxylate (277 mg, 46% yield) as a tan oil.

Step G: Preparation of (1E,4E)-ethyl 2-amino-8-(4-(pyrrolidine-1-carbonyl)phenyl)-3H-benzo[b]azepine-4-carboxylate (24): (1E,4E)-ethyl-2-(tert-butoxycarbonyl)-8-(4-(pyrrolidine-1-carbonyl)phenyl)-3H-benzo[b]azepine-4-carboxylate (110 mg, 0.218 mmol) was diluted with a 1:4 TFA:CH$_2$Cl$_2$ solution (4 mL). The reaction was stirred at room temperature for 1 hour, and then diluted with CH$_2$Cl$_2$. The organic phase was washed with 10% K$_2$CO$_3$ and brine (30 mL). The CH$_2$Cl$_2$ solution was dried over Na$_2$SO$_4$, filtered, and concentrated to provide (1E, 4E)-ethyl 2-amino-8-(4-(pyrrolidine-1-carbonyl)phenyl)-3H-benzo[b]azepine-4-carboxylate (88 mg, 81% yield) as a yellow solid. $^1$H NMR (CDCl$_3$) δ 1.39 (t, 3H), 1.88-1.99 (m, 4H), 2.98 (s, 2H), 3.49-3.52 (m, 2H), 3.66-3.69 (m, 2H), 4.30-4.35 (m, 2H), 7.32 (d, 1H), 7.46-7.49 (m, 2H), 7.60 (d, 2H) 7.67 (d, 2H), 7.84 (s, 1H).

Example 8

Synthesis of (1E,4E)-ethyl 2-amino-8-(4-(methoxycarbonyl)phenyl)-3H-benzo[b]azepine-4-carboxylate (25)

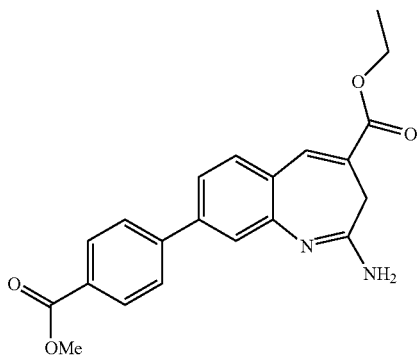

Compound (25) was prepared according to the general procedures described in Example 7, substituting 4-(methoxycarbonyl)phenylboronic acid for 4-(pyrrolidine-1-carbonyl)phenylboronic acid, to provide (1E,4E)-ethyl 2-amino-8-(4-(methoxycarbonyl)phenyl)-3H-benzo[b]azepine-4-carboxylate (17 mg, 0.031 mmol, 54% yield) as a yellow solid. $^1$H NMR (CDCl$_3$) δ 1.39 (t, 3H), 2.99 (s, 2H), 3.94 (s, 3H), 4.32 (q, 2H), 7.33 (dd, 1H), 7.46-7.49 (m, 2H), 7.71 (dd, 2H), 7.83 (s, 1H), 8.09 (s, 1H), 8.11 (s, 1H).

Example 9

Synthesis of (1E,4E)-ethyl 2-amino-8-(4-(methylcarbamoyl)phenyl)-3H-benzo[b]azepine-4-carboxylate (26)

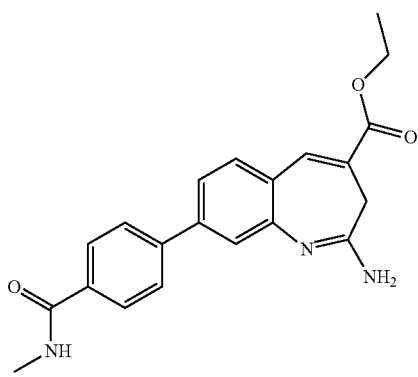

Compound (26) was prepared according to the general procedures described in Example 7, substituting 4-(methylcarbamoyl)phenylboronic acid for 4-(pyrrolidine-1-carbonyl)phenylboronic acid, to provide (1E,4E)-ethyl 2-amino-8-(4-(methoxycarbonyl)phenyl)-3H-benzo[b]azepine-4-carboxylate (1 mg, 0.031 mmol, 21% yield) as a yellow solid.

$^1$H NMR (CDCl$_3$) δ 1.39 (t, 3H), 2.98 (s, 2H), 3.06 (s, 3H), 4.31-4.36 (q, 2H), 7.33 (dd, 1H), 7.46-7.49 (m, 2H), 7.34 (d, 1H), 7.47-7.52 (m, 3H), 7.32 (d, 2H) 7.83-7.85 (m, 3H).

Example 10

Synthesis of (1E,4E)-2-amino-N,N-dipropyl-8-(4-(pyrrolidine-1-carbonyl)phenyl)-3H-benzo[b]azepine-4-carboxamide (27)

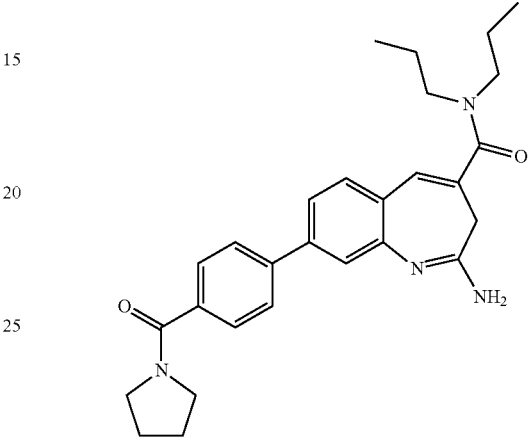

Compound (27) was prepared from compound (24) by a method similar to that described in Example 2 to provide 49 mg (43%) of the desired compound. $^1$H NMR (CDCl$_3$) δ 0.93 (t, 6H), 1.63-1.71 (m, 4H), 1.89 (m, 2H), 1.98 (m, 2H), 2.83 (s, 2H), 3.40-3.51 (m, 6H), 3.67 (t, 2H), 6.83 (s, 1H), 7.3 (dd, 1H), 7.35 (d, 1H), 7.49 (d, 1H), 7.64 (q, 4H).

The activity of the compounds of this invention may be determined by the following assays.

Example 11

HEK/TLR Assays

Human embryonic kidney (HEK) cells which stably express various human TLR genes, including TLR7 and TLR8, and a NFkB-luciferase reporter gene were incubated with various concentrations of compound overnight. The amount of induced luciferase was measured by reading the absorbance at 650 nm. Compounds of this invention have an MC$_{50}$ of 100 μM or less, wherein MC$_{50}$ is defined as the concentration at which 50% of maximum induction is seen.

Example 12

PBMC Assays for TLR7 and TLR8

Peripheral blood mononuclear cells (PBMCs) from human blood were isolated using BD Vacutainer Cell Preparation Tubes with sodium citrate. Cells were incubated with compound overnight. TLR8 activity was assayed by measuring the amount of TNFα in supernatants by ELISA. TLR7 activity was assayed by measuring the amount of IFNα in supernatants by ELISA (R&D Systems). Compounds of this invention had an MC$_{50}$ of 100 μM or less, wherein MC$_{50}$ is the concentration at which 50% of the maximum induction is seen.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A method of treating cancer, comprising administering to a mammal in need thereof an effective amount of a compound of the Formula

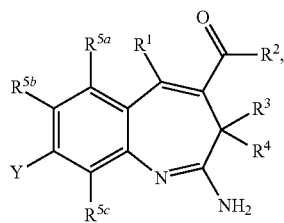

a tautomer, or a pharmaceutically acceptable salt thereof, wherein:

said cancer is selected from biliary tract cancer, brain cancer, breast cancer, cervical cancer, choriocarcinoma, colon cancer, endometrial cancer, esophageal cancer, gastric cancer, intraepithelial neoplasms, leukemia, lymphoma, liver cancer, lung cancer, melanoma, neuroblastomas, oral cancer, ovarian cancer, pancreatic cancer, prostate cancer, rectal cancer, renal cancer, sarcomas, skin cancer, testicular cancer, thyroid cancer, other carcinomas and sarcomas;

Y is an aryl or heteroaryl ring, wherein said aryl and heteroaryl rings are substituted with one or more groups independently selected from alkenyl, alkynyl, Br, CN, OH, $NR^6R^7$, $C(=O)R^8$, $NR^6SO_2R^7$, $(C_1$-$C_6$ alkyl) amino, $R^6OC(=O)CH=CH$—, $SR^6$ and $SO_2R^6$, and wherein said aryl and heteroaryl rings are optionally further substituted with one or more groups independently selected from F, Cl, $CF_3$, $CF_3O$—, $HCF_2O$—, alkyl, heteroalkyl and ArO—;

$R^1$, $R^3$ and $R^4$ are independently selected from H, alkyl, alkenyl, alkynyl, heteroalkyl, cycloalkyl, cycloalkenyl, heterocycloalkyl, aryl and heteroaryl, wherein said alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1$-$C_6$ alkyl)amino, $CH_3OCH_2O$—, $R^6OC(=O)CH=CH$—, $NR^6SO_2R^7$, $SR^6$ and $SO_2R^6$, or $R^3$ and $R^4$ together with the atom to which they are attached form a saturated or partially unsaturated carbocyclic ring, wherein said carbocyclic ring is optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1$-$C_6$ alkyl)amino, $CH_3OCH_2O$—, $R^6OC(=O)CH=CH$—, $NR^6SO_2R^7$, $SR^6$ and $SO_2R^6$;

$R^2$ and $R^8$ are independently selected from H, $OR^6$, $NR^6R^7$, alkyl, alkenyl, alkynyl, heteroalkyl, cycloalkyl, cycloalkenyl, heterocycloalkyl, aryl and heteroaryl, wherein said alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1$-$C_6$ alkyl)amino, $CH_3OCH_2O$—, $R^6OC(=O)CH=CH$—, $NR^6SO_2R^7$, $SR^6$ and $SO_2R^6$;

$R^{5a}$, $R^{5b}$, and $R^{5c}$ are independently H, F, Cl, Br, I, OMe, $CH_3$, $CH_2F$, $CHF_2$ or $CF_3$; and $R^6$ and $R^7$ are independently H, alkyl, or heteroalkyl, such that said cancer is treated.

2. The method of claim 1, wherein said cancer is colon cancer, ovarian cancer, breast cancer, or lymphoma.

3. The method of claim 1, wherein $R^2$ is $OR^6$.

4. The method of claim 3, wherein $R^6$ is alkyl.

5. The method of claim 4, wherein $R^6$ is ethyl.

6. The method of claim 1, wherein $R^2$ is $NR^6R^7$.

7. The method of claim 1, wherein $R^6$ and $R^7$ are independently H, ethyl, propyl, or $CH_2CH_2OCH_3$.

8. The method of claim 1, wherein Y is aryl.

9. The method of claim 8, wherein said aryl is substituted with $C(=O)R^8$.

10. The method of claim 9, wherein $R^8$ is $OR^6$, $NR^6R^7$ or heterocycloalkyl.

11. The method of claim 10, wherein $R^6$ and $R^7$ are independently selected from H and alkyl.

12. The method of claim 1, wherein Y is

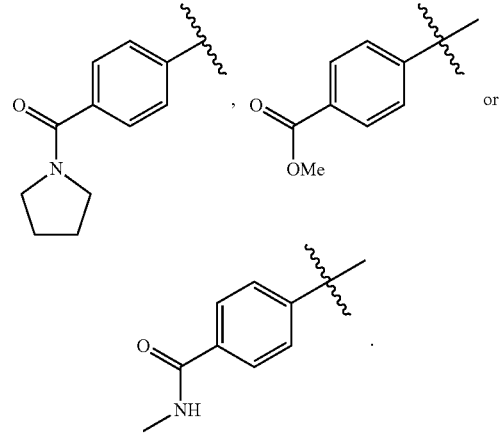

13. The method of claim 1, wherein $R^1$, $R^3$, $R^4$, $R^{5a}$, $R^{5b}$ and $R^{5c}$ are each hydrogen.

14. The method of claim 1, wherein said compound is selected from:

(1E,4E)-ethyl 2-amino-8-(4-(pyrrolidine-1-carbonyl)phenyl)-3H-benzo[b]azepine-4-carboxylate;

(1E,4E)-ethyl 2-amino-8-(4-(methoxycarbonyl)phenyl)-3H-benzo[b]azepine-4-carboxylate;

(1E,4E)-ethyl 2-amino-8-(4-(methylcarbamoyl)phenyl)-3H-benzo[b]azepine-4-carboxylate;

(1E,4E)-2-amino-N,N-dipropyl-8-(4-(pyrrolidine-1-carbonyl)phenyl)-3H-benzo[b]azepine-4-carboxamide; and pharmaceutically acceptable salts thereof.

15. The method of claim 1, wherein said effective amount is about 0.5 to about 35 mg/kg/day.

16. A method of treating allergy, comprising administering to a mammal in need thereof an effective amount of a compound of the Formula

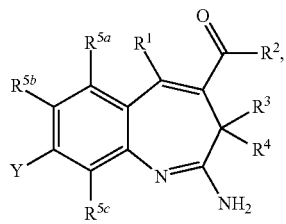

a tautomer, or a pharmaceutically acceptable salt thereof, wherein:

Y is an aryl or heteroaryl ring, wherein said aryl and heteroaryl rings are substituted with one or more groups independently selected from alkenyl, alkynyl, Br, CN, OH, $NR^6R^7$, $C(=O)R^8$, $NR^6SO_2R^7$, $(C_1-C_6$ alkyl)amino, $R^6OC(=O)CH=CH-$, $SR^6$ and $SO_2R^6$, and wherein said aryl and heteroaryl rings are optionally further substituted with one or more groups independently selected from F, Cl, $CF_3$, $CF_3O-$, $HCF_2O-$, alkyl, heteroalkyl and ArO—;

$R^1$, $R^3$ and $R^4$ are independently selected from H, alkyl, alkenyl, alkynyl, heteroalkyl, cycloalkyl, cycloalkenyl, heterocycloalkyl, aryl and heteroaryl, wherein said alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1-C_6$ alkyl)amino, $CH_3OCH_2O-$, $R^6OC(=O)CH=CH-$, $NR^6SO_2R^7$, $SR^6$ and $SO_2R^6$, or $R^3$ and $R^4$ together with the atom to which they are attached form a saturated or partially unsaturated carbocyclic ring, wherein said carbocyclic ring is optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1-C_6$ alkyl)amino, $CH_3OCH_2O-$, $R^6OC(=O)CH=CH-$, $NR^6SO_2R^7$, $SR^6$ and $SO_2R^6$;

$R^2$ and $R^8$ are independently selected from H, $OR^6$, $NR^6R^7$, alkyl, alkenyl, alkynyl, heteroalkyl, cycloalkyl, cycloalkenyl, heterocycloalkyl, aryl and heteroaryl, wherein said alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1-C_6$ alkyl)amino, $CH_3OCH_2O-$, $R^6OC(=O)CH=CH-$, $NR^6SO_2R^7$, $SR^6$ and $SO_2R^6$;

$R^{5a}$, $R^{5b}$, and $R^{5c}$ are independently H, F, Cl, Br, I, OMe, $CH_3$, $CH_2F$, $CHF_2$ or $CF_3$; and $R^6$ and $R^7$ are independently H, alkyl, or heteroalkyl, such that said allergy is treated.

17. The method of claim 16, wherein said allergy is acquired hypersensitivity to an allergen.

18. The method of claim 17, wherein said allergy is selected from eczema, allergic rhinitis or coryza, hay fever, asthma, urticaria (hives) and food allergies, and other atopic conditions.

19. The method of claim 16, wherein said compound is selected from:
(1E,4E)-ethyl 2-amino-8-(4-(pyrrolidine-1-carbonyl)phenyl)-3H-benzo[b]azepine-4-carboxylate;
(1E,4E)-ethyl 2-amino-8-(4-(methoxycarbonyl)phenyl)-3H-benzo[b]azepine-4-carboxylate;
(1E,4E)-ethyl 2-amino-8-(4-(methylcarbamoyl)phenyl)-3H-benzo[b]azepine-4-carboxylate;
(1E,4E)-2-amino-N,N-dipropyl-8-(4-(pyrrolidine-1-carbonyl)phenyl)-3H-benzo[b]azepine-4-carboxamide; and
pharmaceutically acceptable salts thereof.

20. The method of claim 16, wherein said effective amount is about 0.5 to about 35 mg/kg/day.

* * * * *